(12) United States Patent
Goodin et al.

(10) Patent No.: US 7,691,116 B2
(45) Date of Patent: Apr. 6, 2010

(54) CUTTING BLADE FOR MEDICAL DEVICES

(75) Inventors: Richard L. Goodin, Blaine, MN (US); Robert Burgmeier, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 850 days.

(21) Appl. No.: 11/371,408

(22) Filed: Mar. 9, 2006

(65) Prior Publication Data

US 2007/0213752 A1    Sep. 13, 2007

(51) Int. Cl.
    A61B 17/22    (2006.01)
(52) U.S. Cl. .................................................. 606/159
(58) Field of Classification Search .............. 606/159, 606/80, 81, 84, 85, 161, 162, 167, 170, 180; 30/346.61, 351, 303, 350, 346.5, 346.54, 30/346.55, 346.58; 604/103.08
See application file for complete search history.

(56) References Cited

U.S. PATENT DOCUMENTS

| | | | | |
|---|---|---|---|---|
| 1,083,026 A * | 12/1913 | Ohlsson | .......................... | 30/53 |
| 1,813,470 A * | 7/1931 | Thompson | ............... | 30/346.54 |
| 2,125,502 A * | 8/1938 | Holtzman | ................ | 30/346.61 |
| 2,322,744 A * | 6/1943 | Benjamin | ................ | 30/346.61 |
| 2,363,894 A * | 11/1944 | Muros | ........................... | 30/65 |
| 2,413,863 A * | 1/1947 | Connolly | ........................ | 30/70 |
| 3,066,411 A * | 12/1962 | Gore | .............................. | 30/30 |
| 4,273,128 A | 6/1981 | Lary | ........................... | 128/305 |
| 4,781,186 A * | 11/1988 | Simpson et al. | .............. | 606/171 |
| 5,007,896 A * | 4/1991 | Shiber | ........................... | 604/22 |
| 5,047,040 A * | 9/1991 | Simpson et al. | .............. | 606/159 |
| 5,156,610 A | 10/1992 | Reger | .......................... | 606/159 |
| 5,178,625 A * | 1/1993 | Groshong | .................... | 606/159 |
| 5,196,024 A * | 3/1993 | Barath | ......................... | 606/159 |
| 5,226,909 A * | 7/1993 | Evans et al. | .................. | 606/159 |
| 5,312,425 A * | 5/1994 | Evans et al. | .................. | 606/159 |
| 5,314,407 A | 5/1994 | Auth | ............................ | 604/22 |
| 5,320,634 A * | 6/1994 | Vigil et al. | .................... | 606/159 |
| 5,403,334 A * | 4/1995 | Evans et al. | .................. | 606/159 |
| 5,569,277 A * | 10/1996 | Evans et al. | .................. | 606/159 |
| 5,616,149 A * | 4/1997 | Barath | ......................... | 606/159 |
| 5,695,506 A * | 12/1997 | Pike et al. | .................... | 606/159 |
| 4,842,579 A | 6/1999 | Shibert | ........................ | 605/22 |
| 6,019,772 A * | 2/2000 | Shefaram et al. | ............ | 606/159 |
| 6,942,680 B2 * | 9/2005 | Grayzel et al. | .............. | 606/194 |
| 7,011,670 B2 * | 3/2006 | Radisch, Jr. | .................. | 606/159 |
| 7,172,609 B2 * | 2/2007 | Radisch, Jr. | .................. | 606/159 |
| 7,291,158 B2 * | 11/2007 | Crow et al. | ................... | 606/159 |
| 2002/0010489 A1 * | 1/2002 | Grayzel et al. | .............. | 606/194 |
| 2003/0144683 A1 * | 7/2003 | Sirhan et al. | ................. | 606/194 |

(Continued)

FOREIGN PATENT DOCUMENTS

DE        24 02 573 A1      8/1985

(Continued)

*Primary Examiner*—Todd E Manahan
*Assistant Examiner*—Erin Colello
(74) *Attorney, Agent, or Firm*—Crompton, Seager & Tufte, LLC.

(57) ABSTRACT

An athertome assembly comprises a series of spanning and descending members extended between a segmented base and a cutting surface. This athertome assembly configuration provides both flexibility and structural strength which facilitates the implantation of medical devices.

22 Claims, 2 Drawing Sheets

U.S. PATENT DOCUMENTS

| | | | |
|---|---|---|---|
| 2003/0163148 A1* | 8/2003 | Wang et al. | 606/159 |
| 2004/0098014 A1* | 5/2004 | Flugelman et al. | 606/192 |
| 2004/0133223 A1 | 7/2004 | Weber | 623/1.11 |
| 2004/0193196 A1 | 9/2004 | Appling | 623/1.11 |
| 2004/0230178 A1 | 11/2004 | Wu | 606/159 |
| 2004/0243156 A1* | 12/2004 | Wu et al. | 606/159 |
| 2004/0243158 A1* | 12/2004 | Konstantino et al. | 606/159 |
| 2005/0038383 A1 | 2/2005 | Kelley | 606/159 |
| 2005/0080478 A1* | 4/2005 | Barongan | 623/1.14 |
| 2005/0119678 A1 | 6/2005 | O'Brien | 606/159 |
| 2005/0137615 A1* | 6/2005 | Mapes et al. | 606/159 |
| 2005/0222594 A1 | 10/2005 | Maschke | 623/1.11 |
| 2005/0228343 A1* | 10/2005 | Kelley | 604/96.01 |

FOREIGN PATENT DOCUMENTS

| | | |
|---|---|---|
| DE | 3402573 A1 * | 8/1985 |
| WO | 2005/099584 A1 | 10/2005 |

* cited by examiner

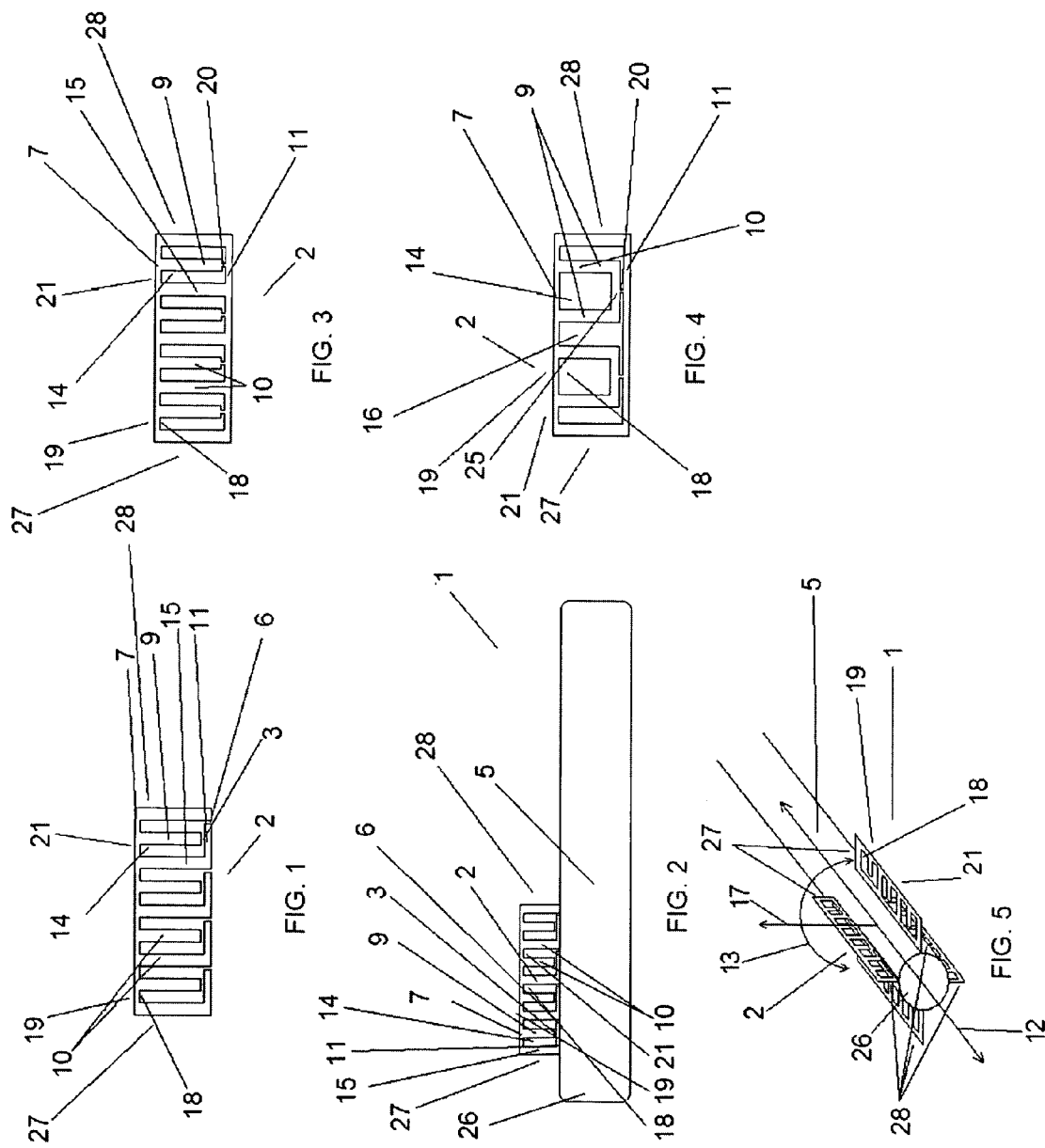

CUTTING BLADE FOR MEDICAL DEVICES

CROSS-REFERENCE TO RELATED APPLICATIONS

Not Applicable

STATEMENT REGARDING FEDERALLY SPONSORED RESEARCH

Not Applicable

FIELD OF THE INVENTION

In some embodiments this invention relates to implantable medical devices, their manufacture, and methods of use in particular atherectomy devices.

DESCRIPTION OF THE RELATED ART

Stents, grafts, stent-grafts, vena cava filters, expandable frameworks, and similar implantable medical devices are radially expandable endoprostheses which are typically intravascular implants capable of being implanted transluminally and enlarged radially after being introduced percutaneously. These endoprostheses may be implanted in a variety of body lumens or vessels such as within the vascular system, urinary tracts, bile ducts, fallopian tubes, coronary vessels, secondary vessels, etc. Some endoprostheses such as stents may be used to reinforce body vessels and to prevent restenosis following angioplasty in the vascular system. Endoprostheses may be self-expanding, expanded by an internal radial force, such as when mounted on a balloon, or a combination of self-expanding and balloon expandable (hybrid expandable).

Insertion of an implantable medical device can be facilitated by the attachment of one or more cutting tools to the radially compressed device. These tools, frequently called atherectomy devices or athertomes, typically comprise a blade, cutting bit, burr, and/or other surface protrusions on at least a portion of the flexible drive shaft, catheter, or stent. Athertomes can be contained within flexible sheaths to protect the walls of the blood vessels from the rotation of the implantable medical device. Athertomes can be attached to medical devices including but not limited to stents, balloons, grafts, catheters, and sheaths. Examples of such devices include Barath, U.S. Pat. No. 5,196,024, Shiber, U.S. Pat. No. 4,842,579, Simpson et al., U.S. Pat. No. 5,047,040; and Auth et al., U.S. Pat. No. 5,314,407, incorporated herein by reference. The atherectomy device is typically navigated to the site of the disease by a delivery system such as a mechanically manipulated guide wire to the site of the disease, and then the atheretome is advanced over the guide wire to the site.

The navigation of the guide wire through the blood vessel can be a slow and tedious process, requiring great skill. It can be difficult to precisely control the atherectomy device satisfactorily. Part of this difficulty arises from rigidity of the blades which do not bend as readily as balloons, stents, wires and other components of implantable devices when traversing the wending paths of body vessels.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

At least one possible embodiment of the invention is directed to an athertome assembly comprising at least one segment having at least one base member and at least one cutting member in which the cutting member has a first and a second side, at least a portion of the first side having a cutting surface. The at least one segment also has at least one descending member and at least one spanning member which at least partially define a through hole located between the at least one descending member and the at least one spanning member. The at least one spanning member is engaged at one end to the second side of the at least one cutting member and engaged at another end to the at least one base member. The at least one descending member is engaged at one end to the second side of the at least one cutting member and extends in the direction of the at least one base member but is not engaged to the at least one base member.

The athertome assembly can be constructed in a number of variations. These variations include having a plurality of descending members, having a plurality of spanning members, having uninterrupted cutting surfaces, having non-adjacent base members, and having narrow connectors linking adjacent members. The connectors themselves can be positioned in various ways including at the center of a horizontal members.

At least some possible embodiments of the invention are directed to a medical system having at least one athertome assembly engaged to at least one medical device. In some instances, the athertome assembly may be disposed on the medical device such that an imaginary plane perpendicular to the central longitudinal axis of the medical device passes through a cutting member, a base member and a descending member of the athertome. Appropriate medical devices include but are not limited to stents, catheters, balloons, sheaths, grafts, and combinations of these devices. The athertome assembly can be engaged to a medical device in a variety of ways including the following: Multiple athertomes assemblies can be engaged to a medical device. In some possible embodiments three or four athertome assemblies will be engaged to a medical device. The multiple athertome assemblies can be located at positions substantially equidistant from each other or in non-symmetrical relative positions. They can also be positioned at different locations relative to the terminal end of the medical device. They can extend along the surface of a medical device along a number of paths including longitudinal, perpendicular, and diagonal paths. They or portions of them can have cutting surfaces positioned at differing distances from the surface of medical device. They can be non-linear and/or can coil around the medical device in a helical direction. In addition, they can be flexibly engaged to the medical device and can pivot and change the angle they form with the medical device.

BRIEF DESCRIPTION OF THE SEVERAL VIEWS OF THE DRAWING(S)

A detailed description of the invention is hereafter described with specific reference being made to the drawings.

FIG. 1 is a view of an athertome having unconnected base members.

FIG. 2 is a view of an athertome assembly having an athertome connected to the outer surface of a medical device.

FIG. 3 is a view of an athertome having descending members connected to the base member by connectors.

FIG. 4 is a view of an athertome having horizontal members connecting descending members.

FIG. 5 is a perspective view of a catheter having four athertomes engaged to it.

DETAILED DESCRIPTION OF THE INVENTION

Figure 6:
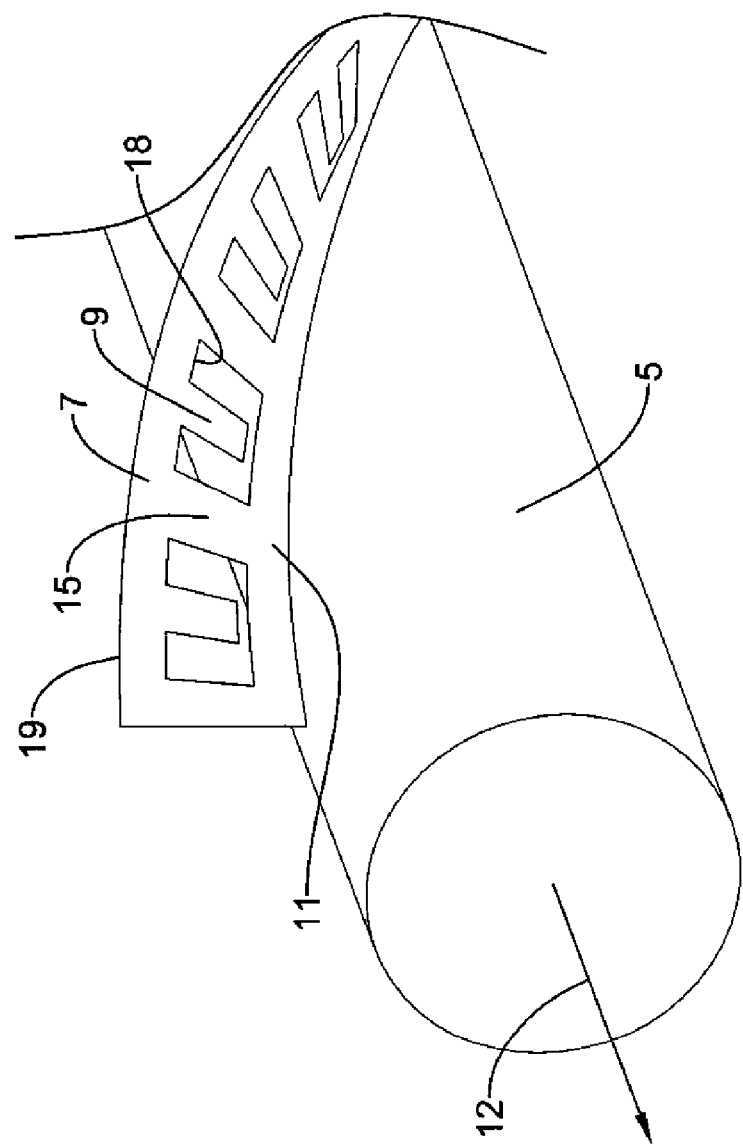
FIG. 6 is a perspective view of an athertome assembly including a helically arranged athertome.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Depicted in the figures are various aspects of the invention. Elements depicted in one figure may be combined with, and/or substituted for, elements depicted in another figure as desired.

Referring now to FIG. 1 there is shown an athertome 2 having a first end 27 and a second end 28 made up of a plurality of segments. Each segment is made up of a cutting member 7 which is opposite one or more base members 11. The cutting member 7 has two sides, an inner side 18 which is engaged to other athertome members and cutting side 19. At least a portion of the cutting side 19 defines the cutting surface 21 of the athertome 2. Extending between the cutting member 7 and the base members 11 are crossing members 10, some of which are descending members 9 which do not reach all the way to the base members 11 and some of which are spanning members 15 which reach and are engaged to the base members 11. Separating the descending members 9 and spanning members 15 are through holes 14. The through holes 14 are apertures extending completely though the athertome material. Although in this illustration, the cutting member 7 and the base members 11 are parallel with each other this need not be the case. This invention encompasses embodiments having an athertome 2 of any conceivable shape including but not limited to square, rectangular, triangular, rhomboid, etc. Similarly, some or all of the crossing members 10 need not be perpendicular to the base 11 or cutting members 7 and can be oriented at any oblique angle relative to the base 11 or cutting members 7. This invention also encompasses possible embodiments where at least a portion of members other than the cutting member 7 can also have cutting surfaces. Although FIG. 1 illustrates an athertome where spanning members 15 define the two ends of the athertome 2, this invention encompasses possible embodiments where the ends are defined by other members or features of the athertome 2. In addition this athertome 2 encompasses possible embodiments where the first and second ends 27, 28 also have cutting surfaces.

In the embodiment shown, the cutting members 7 of each segment are all interconnected and form one continuous and uninterrupted cutting member 7 extending along the length of the athertome 2. In the embodiment shown in FIG. 1, the base of the athertome is not a single structure, but is instead a series of base members 11 with base gaps 6 between each base member. The embodiment also features descending gaps 3 between every other descending member 9 and a base member 11. As with the through holes 14, the base gaps 6 and the descending gaps 3 are apertures extending completely through the material of the athertome 2. The presence of the base gaps 6 and the descending gaps 3 facilitates flexing and bending of the athertome 2 relative to the medical device it is engaged to. This flexibility in turn facilitates the advancement of the delivery system carrying the medical device and the athertome assembly 1 through the tortuous confines of a body vessel or other lumen. This invention also encompasses embodiments where only a portion of the athertome 2 or only one segment has a continuous and uninterrupted cutting surface or only a portion of the athertome 2 has base gaps 6 and descending gaps 3.

An illustration of one possible embodiment where the athertome 2 of FIG. 1 is engaged to a medical device 5 by the base members 11 is shown in FIG. 2. The types of medical devices capable of supporting mounted athertomes include but are not limited to stents, sheaths, grafts, shafts, catheters, balloons or any combination of medical devices. The athertome can be a separate part attached to a portion of a medical device or it can be an integrated component of the device created out of the same material as the medical device. Although FIG. 2 shows the athertome 2 located relatively close to the terminal end 26 of the medical device 5, this invention encompasses embodiments where the athertome 2 is located anywhere along the medical device 5.

Similarly, although this illustration shows a single athertome 2 attached to the medical device 5, any number of athertomes 2 may be a part of, may be engaged to, or may protrude from an implantable medical device. In at least one possible embodiment for example, at least three or four athertomes 2 are radially affixed or otherwise engaged to a medical device such as a balloon or an implantable stent. The radially positioned athertomes can be equidistant to each other relative to the circumferential cross section of the medical device or they can be positioned at unequal intervals relative to the circumferential cross section of the medical device.

In one embodiment, when engaged to a medical device, the athertomes 2 are not in a rigidly radial deployed position and can change the angle they form relative to the surface of the medical device. The athertomes 2 can both self deploy and retract down on to the surface of the medical device as needed through the expansion of the medical device or through an independent expansion or retraction mechanism.

In embodiments having multiple athertomes 2, the athertomes may be positioned in a uniform or non-uniform distribution about the medical device. In some possible embodiments, different kinds of athertomes 2 (including but not limited to athertomes known in the art, and/or those illustrated in FIGS. 1, 3, and 4) may be affixed to, may protrude from, or may be otherwise engaged to a medical device 5. Although FIGS. 2 and 5 show the athertomes extending along the medical device in a longitudinal configuration, at least a portion of an athertome 2 can also coil around the device in a helical configuration as shown in FIG. 6, can extend around circumference of the device or can be positioned with any combination of these configurations. In addition, the cutting member or members 7 need not be of uniform distance from the surface of the medical device 26 and differing portions of the cutting member 7 can be closer or farther away from the surface of the medical device 5. The cutting member 7 of the athertome 2 can taper downwards towards the terminal end 26 or downwards away from the terminal end 26. The cutting member 7 can also be serrated. This invention encompasses possible embodiments where the athertomes are positioned along the medical device in a fixed rigid position as well as embodiments where the athertomes can deploy and retract relative to the medical device.

Referring again to FIG. 1, there is shown a particular embodiment where most of the segments of the athertome 2 comprise at least one descending member 9 and at least one spanning member 15 between the cutting member 7 and the base members 11. The spanning members 15 connect the base members 11 to the cutting member 7. Alongside the spanning members 15 are descending members 9 which are connected to the cutting member 7 but not the base members 11. The descending members 9 provide the cutting surface with additional support when the athertome 2 is used for cutting but because they are disconnected from the base members 11, they allow for more flexibility than if they were rigidly connected. Although FIG. 1 illustrates an embodiment where the segments are virtually identical and regularly repeat, the invention is also directed to embodiments where the segments are not identical and the athertome 2 comprises segments with different shapes and with different numbers of crossing members. In addition, the invention encompasses embodiments where some or even all of the base members 11 are interconnected or where some or all of the crossing members of segments are connected to the base members 11.

FIG. 1 illustrates one possible embodiment where the athertome 2 has descending members 9 and spanning members 15 which extend in a direction forming a 90 degree angle relative to the base members 11 and the cutting member 7. This invention however also encompasses embodiments where the spanning members 15 and the descending members 9 form oblique angles relative to the cutting member 7, relative to the base members 11, or relative to both. For purposes of this application the term "oblique" refers to an angle of between 0 and 180 degrees (according to an inclusive range) and explicitly includes angles of 30, 45, 60, and 90 . . . etc. degrees. This invention also encompasses embodiments where the descending members 9, the spanning members 15, the through hole 14, the cutting member 7, and the base members 11 are not of a generally rectangular shape.

Referring now to FIG. 3 there is shown another athertome 2 made up of a plurality of segments. In this embodiment, at least some of the segments comprise a spanning member 15 and a descending member 9 where the descending member 9 is connected to the base member 11 by a connector 20. The figure also has spanning members 15 defining both ends of the athertome 2. The descending member is substantially wider than the connector 20. Unlike the embodiment of FIG. 1, a segment in this embodiment has no descending gaps between the descending members and the base members. Because of the difference in width between the connector 20 and the descending member 9, this embodiment affords the athertome flexibility but the connectors provide the athertome 2 with structural strength. Because a connected descending member 9 does not have as great a range of motion that an unconnected descending member 9 would, this embodiment is not as flexible as the one illustrated in FIG. 1. However, because of the connections 20, this embodiment has greater structural strength than does the embodiment of FIG. 1. This embodiment contemplates an athertome 2 in which some of the segments contain the attributes of the athertome as described in the descriptions of FIGS. 1, 2, and 5.

The embodiment illustrated in FIG. 3 also has greater structural strength and less flexibility than the embodiment of FIG. 1 because it has single base member 11. The flexibility and structural strength of this embodiment however can be modified by altering the nature of some or all of the athertome segments. The flexibility can be increased by having segments with multiple unconnected base members 11 and/or unconnected descending members 9. The base members can also be connected by connectors with smaller widths than the widths of the base members 11. This invention also encompasses embodiments where the descending and spanning members between the cutting member 7 and the base members 11 of each segments is non-uniform and irregular.

Referring now to FIG. 4 there is shown another athertome 2 made up of a plurality of segments. In this embodiment, at least some of the segments comprise two descending members 9 connected by a horizontal member 25. The horizontal member 25 is connected to the base member 11 by a connector 20 and further defines the through hole 14. Although FIG. 4 illustrates the connector 20 positioned at the center of the horizontal member 25 this invention encompasses possible embodiments where the connector 20 is positioned anywhere along the horizontal member 25. Because of the narrow width of the connector 20 relative to the width of the descending members 9, and because there is only one connector for every two descending members 9, this design is highly flexible. The horizontal members 25 however provide this embodiment with structural strength.

The embodiments disclosed by the various drawings provide for athertomes with a number of superior properties. The unconnected descending members 9 and non-connecting base members 11 such as those illustrated in FIG. 1 afford the athertome a wide range of motions resulting in a high degree of flexibility. The improved flexibility allows for the athertome undergo multidimensional bending. The multidimensional bend paths are illustrated in FIG. 5. They include bend paths along any possible combination of some or all of; the longitudinal axis 12, the transverse axis 17 perpendicular to the longitudinal axis 12, and along the circumferential arc 13.

This high degree of flexibility allows for a number of advantages to the athertome. Because it can bend to accommodate the tortuous curves of body vessels, the athertome can be more easily tracked through the body. This flexibility also allows the athertome to more easily pass through or interact with other devices associated with a medical procedure (such as passing through a guiding catheter). In addition, because the flexible athertome is less likely to straighten or otherwise deform body vessels such as arteries when being tracked through them, it is less likely to cause certain unwanted side effects. The improved flexibility also allows the athertome to be created with a greater thickness or out of a denser or harder material which would otherwise be too rigid to be practical. The presence of a greater thickness or a denser or harder material provides the athertome with an increase in cutting force. Finally, the greater flexibility allows for easier insertion and removal of the athertome as it can be moved, pulled, or pushed through a body vessel with less force.

In certain circumstances, an athertome with some flexibility, but with more physical strength than that of FIG. 1 may be desired. The flexible athertome of FIG. 4 is more rigid (and physically strong) than that of FIG. 1 and the flexible athertome of FIG. 3 is more rigid (and physically strong) than that of FIG. 4. The inventive concept contemplates embodiments where athertomes contain a combination of some or all of the features of FIGS. 1, 3, and 4. This resulting combination can be made to modulate the rigidity, strength, or flexibility of the athertome to a desired level and can cause a desired amount of rigidity, strength, or flexibility to be associated with an entire athertome or to a particular region of an athertome.

The athertomes illustrated in FIGS. 1-6 may be created by methods including laser cutting, etching a design from a stock, cutting a flat sheet of material and stamping with a stamping die. These methods remove the excess material from the resulting athertome to form the base gaps, the descending gaps the through holes, and the open spaces between the members and the segments as illustrated in FIGS. 1-5. By creating these various openings and spaces, a very flexible but sufficiently strong athertome is provided. By increasing the loss of material (i.e. by making the members thinner and making the openings, spaces, and gaps wider) a lighter more streamlined device can be provided. These athertomes can be created out of such materials including but not limited to metals, polymers, carbon, and nanocomposites. Some specific examples of materials used may include but are not limited to copolymers, polyethylene terephthalate, nylons, polyamides, polyether block amides, thermoplastic polyester elastomers, polyethylene naphthalate, and polyethylene naphthalate elastomers.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A medical device assembly comprising:
   an expandable balloon having a central longitudinal axis; and
   an athertome assembly disposed on the expandable balloon, the athertome assembly comprising:
      at least one segment having at least one base member and at least one cutting member, the culling member having a first and a second side, at least a portion of the first side having a cutting surface, the at least one segment further having at least one descending member and at least one spanning member, a through hole being at least partially defined between the at least one descending member and the at least one spanning member;
      the at least one spanning member engaged at one end to the second side of the at least one cutting member and engaged at another end to the at least one base member; and
      the at least one descending member engaged at one end to the second side of the at least one cutting member and extending in the direction of the at least one base member but not being engaged to the at least one base member;
      wherein an imaginary plane perpendicular to the central longitudinal axis passes through the cutting member, the base member and the at least one descending member.

2. The medical device assembly of claim 1 in which more than one segment share an uninterrupted cutting surface extending along the length of the athertome assembly.

3. The medical device assembly of claim 1 in which the base members of at least two adjacent segments are not immediately adjacent.

4. The medical device assembly of claim 1 in which the base members of at least two adjacent segments are engaged to each other and define an uninterrupted base member.

5. The medical device assembly of claim 1 further comprising at least one connector connecting the at least one descending member to at the least one base member, the at least one connector having a width substantially narrower than a width of the at least one descending member.

6. The medical device assembly of claim 1 in which the athertome assembly has two ends, at least one end defined by the at least one spanning member.

7. The medical device assembly of claim 1, in which the at least one segment further comprises two adjacent descending members each engaged to a horizontal member extending between the two descending members, the horizontal member further defines the through hole, the horizontal member being connected to the base member only by a connector, the connector having a width that is substantially narrower than a width of either of the two descending members.

8. The medical device assembly of claim 7 in which the connector is in the center of the horizontal member.

9. A medical device assembly comprising:
   an expandable balloon having a central longitudinal axis; and an athertome assembly disposed on the expandable balloon, the athertome assembly comprising:
      at least one segment having at least one base member and at least one cutting member, the cutting member having a first and a second side, at least a portion of the first side having a cutting surface, the at least one segment comprising a plurality of descending members and a plurality of spanning members, the descending members and spanning members alternatingly positioned with a through hole being at least partially defined between each descending member and spanning member;
      the spanning members engaged at one end to the second side of the at least one cutting member and engaged at another end to the at least one base member; and
      the descending members engaged at one end to the second side of the at least one cutting member and extending in the direction of the at least one base member but not being engaged to the at least one base member;
      wherein an imaginary plane perpendicular to the central longitudinal axis passes through the cutting member, the base member and at least one descending member.

10. A medical system comprising at least one athertome assembly and at least one medical device having a central longitudinal axis, the at least one medical device being selected from at least one member of the group consisting of a stent, a catheter, a balloon, a sheath, a graft and any combination thereof, the athertome assembly comprising at least one segment having at least one base member and at least one cutting member, the cutting member having a first and a second side, at least a portion of the first side having a cutting surface, the at least one segment further having at least one descending member and at least one spanning member, a through hole being at least partially defined between the at least one descending member and the at least one spanning member;

the at least one spanning member engaged at one end to the second side of the at least one cutting member and engaged at another end to the at least one base member;

the at least one descending member engaged at one end to the second side of the at least one cutting member and extending in the direction of the at least one base member but not being engaged to the at least one base member; and the at least one base member being engaged to a surface of the at least one medical device;

wherein an imaginary plane perpendicular to the central longitudinal axis passes through the cutting member, the base member and the at least one descending member.

11. The medical system of claim 10 in which there are between three and four athertome assemblies engaged to the at least one medical device.

12. The medical system of claim 10 in which there is more than one athertome assembly, where the at least one medical device has a cross sectional circumference and where at least two athertome assemblies are located at positions substantially equidistant from each other relative to the cross sectional circumference.

13. The medical system of claim 10 in which there is more than one athertome assembly, where the at least one medical device comprises a terminal end, and where at least two athertome assemblies are positioned at different distances relative to the terminal end.

14. The medical system of claim 10 in which at least a portion of at the least one athertome assembly extends along the surface of the at least one medical device in a longitudinal direction.

15. The medical system of claim 10 in which at least a portion of the at least one athertome assembly is coiled around the at least one medical device in a helical direction.

16. The medical system of claim 10 in which the distance between the surface of the at least one medical device and the adjacent cutting surface of the at least one athertome assembly at one point along the length of the at least one athertome assembly is different from the distance between the surface of the at least one medical device and the adjacent cutting surface of the at least one athertome assembly at another point along the length of the at least one athertome assembly.

17. The medical system of claim 16 in which the at least one medical device has a terminal end and in which the at least one cutting surface at the end of the at least one athertome assembly closer to the terminal end is closer to the surface of the at least one medical device than the at least one cutting surface at the end of the at least one athertome assembly positioned farther away from the terminal end.

18. The medical system of claim 16 in which the at least one medical device has a terminal end and in which the at least one cutting surface at the end of the at least one athertome assembly closer to the terminal end is farther away from the surface of the at least one medical device than the at least one cutting surface at the end of the at least one athertome assembly positioned farther away from the terminal end.

19. The medical system of claim 10 in which the angle formed between the at least one athertome assembly and the surface of the medical device can change.

20. A medical device assembly comprising:
an expandable balloon having a central longitudinal axis; and
an athertome assembly disposed on the expandable balloon, the athertome assembly comprising:
a) first segment comprising:
  i) a base member;
  ii) a cutting member, the cutting member having a first side and a second side, at least a portion of the first side having a cutting surface;
  iii) a spanning member engaged at one end to the second side of the cutting member and engaged at another end to the base member;
  iv) a descending member engaged at one end to the second side of the cutting member and extending in the direction of the base member but not being engaged to the base member, wherein an imaginary plane perpendicular to the central longitudinal axis passes through the cutting member, the base member and the descending member; and
  v) a through hole being at least partially defined between the descending member and the spanning member; and
b) a second segment comprising:
  i) a base member;
  ii) a cutting member, the cutting member having a first side and a second side, at least a portion of the first side having a cutting surface;
  iii) a spanning member engaged at one end to the second side of the cutting member and engaged at another end to the base member;
  iv) a descending member engaged at one end to the second side of the cutting member and extending in the direction of the base member but not being engaged to the base member, wherein an imaginary plane perpendicular to the central longitudinal axis passes through the cutting member, the base member and the descending member; and
  v) a through hole being at least partially defined between the descending member and the spanning member;
wherein the cutting member of the first segment is continuous with the cutting member of the second segment.

21. The medical device assembly of claim 20, wherein the base member of the first segment is discontinuous with the base member of the second segment, defining a gap between the base member of the first segment and the base member of the second segment.

22. The medical device assembly of claim 20, wherein the cutting surface of the cutting member of the first segment and the cutting surface of the cutting member of the second segment form a continuous and uninterrupted cutting surface.

* * * * *

UNITED STATES PATENT AND TRADEMARK OFFICE
CERTIFICATE OF CORRECTION

PATENT NO. : 7,691,116 B2
APPLICATION NO. : 11/371408
DATED : April 6, 2010
INVENTOR(S) : Richard L. Goodin et al.

It is certified that error appears in the above-identified patent and that said Letters Patent is hereby corrected as shown below:

Column 7
Line 60, delete "culling", and insert therefor -- cutting --.

Signed and Sealed this

First Day of June, 2010

David J. Kappos
*Director of the United States Patent and Trademark Office*